United States Patent [19]

Li

[11] 4,330,465
[45] May 18, 1982

[54] NOVEL β-ENDORPHIN ANALOGS

[75] Inventor: Choh H. Li, Berkeley, Calif.

[73] Assignee: Hoffmann-La Roche Inc., Nutley, N.J.

[21] Appl. No.: 882,719

[22] Filed: Mar. 2, 1978

[51] Int. Cl.$^3$ .......................................... C07C 103/52
[52] U.S. Cl. .............................................. 260/112.5 E
[58] Field of Search ................. 260/112.5 R, 112.5 E

[56] References Cited

U.S. PATENT DOCUMENTS 4,038,222  7/1977  Li ........................................... 260/8

FOREIGN PATENT DOCUMENTS 2716400  11/1977  Fed. Rep. of Germany ... 260/112.5 R

OTHER PUBLICATIONS

Guillemin, et al., Annals of the New York Academy of Sciences 297, 131–157 (1977).
Chem. and Engin. News, Nov. 15, 1976, pp. 26 and 27.
J. Med. Chem. 20 (1977), pp. 325–328.
Proc. 5th Am. Peptide Symposium (1977), pp. 107–110 and 503–505.

*Primary Examiner*—Delbert R. Phillips
*Attorney, Agent, or Firm*—Jon S. Saxe; Bernard S. Leon; James H. Callwood

[57] ABSTRACT

The solid-phase syntheses of [Ala$^2$]-, [D-Leu$^2$]-, [D-Lys$^2$], [Leu$^5$]- and [D-Ala$^2$, D-Leu$^5$] β-endorphins are described. The synthetic peptides were purified by chromatography on carboxymethylcellulose and partition chromatography on Sephadex G-50. They were characterized by partition chromatography on agarose, thin-layer chromatography, paper electrophoresis, and amino acid analyses of acid and enzymic hydrolysates. Bioassay of the synthetic analogs for analgesic activity by the tail-flick-method showed the D-Leu$^2$ analog to be 48% as potent as $\beta_h$-endorphin while the Ala$^2$, D-Lys$^2$, Leu$^5$, and [D-Ala$^2$, D-Leu$^5$] analogs were 8 to 17% as active.

6 Claims, No Drawings

NOVEL β-ENDORPHIN ANALOGS

BACKGROUND OF THE INVENTION

The stereochemical requirements for biological activity in the enkephalin segment, i.e. residues 1-5 of β-endorphin has recently been examined by Yamashiro et al., Int. J. Peptide Protein Res. 10, 159 (1977). Substitution of amino acids in positions 1, 4 and 5 by the corresponding D-isomers resulted in drastic decreases in biological activity for each of the three analogs. On the other hand replacement of glycine in position 2 by D-alanine gave an analog with potency comparable to that of the parent molecule. With the enkephalins this replacement greatly increases analgesic activity. In the report on the isolation of the enkephalins (Hughes et al. Nature (Lond.) 258, 258 (1975) the existence of methionine and leucine forms was noted. A parallel leucine form of β-endorphin has been suggested to have been found in renal dialysis fluid of schizophrenic patients by Dr. Roberta Palmour at the Conference on Endorphins In Mental Health Research in San Juan, Puerto Rico during Dec. 11-13, 1977 after completion of the studies upon which the present application is based.

DESCRIPTION OF THE INVENTION

The present invention relates to the novel β-endorphin analogs [Ala$^2$]-, [D-Lys$^2$]-, [Leu$^5$]- and [D-Ala$^2$, D-Leu$^5$] β-endorphin. These compounds exhibit significant opiate agonist activity and are therefor useful as analgesic agents. A preferred compound of the invention [Leu$^5$]-β-endorphin while having a comparatively lower level of analgesic activity is of particular interest as a selective therapeutic agent for the treatment of mental disease states such as schizophrenia and depression.

The term β-endorphin as used herein is meant to include the various species specific sequences of this compound such as the sequences represented by human β-endorphin ($β_h$-endorphin), ovine or camel β-endorphin ($β_c$-endorphin) and porcine β-endorphin ($β_p$-endorphin).

The solid-phase synthesis (Merrifield, 1963) of protected peptide polymers corresponding to $β_c$-endorphin-(6-31) and $β_h$-endorphin-(6-31) is known in the art. See for example Li et al., J. Med. Chem. 20, 325 (1977) and Yamashiro et al., supra. The corresponding $β_p$-endorphin intermediate can be prepared according to the procedures set forth in U.S. Pat. No. 4,038,222. An aliquot of the appropriate peptide resin was used for synthesis of each of the analogs as indicated in Table I. Synthesis was completed by the same aforementioned procedures in a Beckman 990 peptide synthesizer with use of the following side-chain protecting groups: Z for Tyr (Yamashiro et al., supra) and 2-BrZ for D-Lys (Blake and Li, Int. J. Peptide Protein Res. 8, 589 (1976). The Boc derivatives of D-alanine and D-leucine were used. Each coupling step was performed using symmetrical anhydride as described previously (Li et al., supra and Yamashiro et al., supra. The last Boc group was removed with 50% TFA in $CH_2Cl_2$ for methionine-containing peptides. Removal of all remaining protecting groups and cleavage from the resin was effected in ca. 10 ml liquid HF in the presence of anisole (0.6 ml) at 0° for 75 min. After removal of HF with nitrogen (<0°), the residue was washed with ethyl acetate (25 ml) and the product was extracted with 0.5 N acid (5 ml). Gel filtration was performed in a 2.16×25 cm column of Sephadex G-10 in 0.5 N acetic acid (3 ml fractions). Chromatography on carboxymethylcellulose was performed at 24° on a 1.23×42 cm column with an initial buffer of 0.01 M NH$_4$OAc of pH 4.5 and collection of 10 ml fractions at a flow rate of ca. 200 ml/hr. A gradient with respect to pH and salt concentration was effected through a 500 ml constant volume mixing chamber containing the starting buffer with 0.2 N NH$_4$OAc after fractions no. 10 and 0.4 N NH$_4$OAc after fraction no. 30. The elution position for each analog is indicated in Table I. Partition chromatography on Sephadex G-50 was performed in a 1.76×48 cm column in solvent system A:1-butanol-pyridine-0.6 M NH$_4$OAc (5:3:10) or in a 1.91×30 cm column in solvent system B: 1-butanol-pyridine-0.1 N NH$_4$OH containing 0.1% HOAc (2:1:3) (all ratios and percentages in v/v). The overall yields of the highly purified analogs are recorded in Table I.

TABLE I

Synthesis, Purification, and Characterization of Synthetic β-Endorphin Analogs

| Peptide | Starting Resin[a] | CMC Position in Fraction Nos. | Partition Chromatography on Sephadex G-50 in System A ($R_f$) | Yields[b] | TLC ($R_f$) | Paper Electrophoresis ($R_f^{Lys}$) pH 3.7 | pH 6.9 | Partition Chromatography on Agarose in System A ($R_f$) |
|---|---|---|---|---|---|---|---|---|
| [Sar$^2$]-$β_c$-EP | 50 μmol | 47-48 | 0.26 | 34.3 mg (17%) | 0.48 | 0.65 | 0.53 | 0.148 |
| [Ala$^2$]-$β_c$-EP | 37 | 47 | 0.29 | 33.3 mg (19%) | 0.46 | 0.66 | 0.50 | 0.167 |
| [D-Leu$^2$]-$β_c$-EP | 37 | 48 | 0.51 | 39.9 mg (23%) | 0.50 | 0.66 | 0.50 | 0.34 |
| [D-Lys$^2$]-$β_c$-EP | 35.5 | 54 | 0.37[c] | 43.6 mg (25%) | 0.42 | 0.73 | 0.55 | 0.064 |
| [Pro$^5$]-$β_h$-EP | 50 | 36 | 0.23 | 40.8 mg (17%) | 0.50 | 0.56 | 0.35 | 0.129 |
| [Leu$^5$]-$β_h$-EP | 50 | 35 | 0.51 | 41.9 mg (17%) | 0.54 | 0.56 | 0.35 | 0.27 |
| [D-Leu$^5$]-$β_h$-EP | 83 | 39-40 | 0.58 | 67.0 mg (16%) | 0.56 | 0.56 | 0.35 | 0.32 |
| [D-Ala$^2$, D-Leu$^5$]-$β_h$-EP | 83 | 38 | 0.63 | 56.2 mg (14%) | 0.55 | 0.56 | 0.35 | 0.36 |

[a]Corresponds to load on starting Boc-amino acid resin
[b]Percent yields based on peptide content from amino acid analysis
[c]Run in Solvent System B Each analog was examined by the following criteria: (1) partition chromatography (ca 1 mg) on agarose in a 1.06×20.4 cm column of Bio-Gel A-0.5 m (200–400 mesh) in solvent system A; (2) thin-layer chromatography on silica gel in 1-butanol-pyridine-acetic acid-water (5:5:1:4) with ninhydrin and $Cl_2$-tolidine detection; (3) paper electrophoresis on Whatman 3MM (400 v, 4–6 hr) at pH 3.7 (Pyridine acetate buffer) and at pH 6.9 (collidine acetate buffer) with ninhydrin detection. Each analog was homogeneous with properties shown in Table I.

Amino acid analyses after 24 hr acid hydrolysis are shown in Table II and were in agreement with expected values. For amino acid analysis of total enzyme hydrolysates each peptide was dissolved in 0.05 M Tris buffer of pH 8.5 (0.01 M $Mg^{++}$) to a concentration of 2 mg/ml and treated with trypsin and chymotrypsin (Worthington) with a 50:1 peptide to enzyme weight ratio at 37° for 24 hours. The solution was heated at 100° for 15 minutes. Treatment with leucine aminopeptidase (Worthington) was performed at the 50:1 ratio at 37° for 72 hours. The solution was made 0.1 N in NaOH and lyophilized.

by the tail-flick method. The peptide was injected i.c.v. in a volume of 5 ul according to the method described by Haley and McCormick, Brit. J. Pharmacol. 12, 11 (1957). The median antinociceptive does ($AD_{50}$) and 95% confidence limits were calculated according to the method of Litchfield and Wilcoxon, J. Pharmacol. Exp. Ther. 96, 99 (1949). A two-fold increase in latency of reaction time of tail-flick response observed at 20 and/or 30 minutes after injection was used as a quantal index of inhibition.

The following specific novel analogs of β-endorphin were synthesized by the solid-phase method: [$Ala^2$]-, [$D-Leu^2$]- and [$D-Lys^2$] $β_c$-endorphin and [$Leu^5$]- and [$D-Ala^2$, $D-Leu^5$] $β_h$-endorphin. The selection of either camel or human sequences in an interchangeable manner was based on a previous demonstration that the species variable hormones possess similar potencies in several assay systems. The peptides as indicated above, were purified by chromatography on CMC and partition chromatography on Sephadex G-50 and then characterized by partition chromatography on agarose, thin-layer chromatography, paper electrophoresis in buffers of two pHs, and amino acid analyses of both acid and enzymic hydrolysates.

Since the partition chromatography on agarose was performed in the same biphasic solvent system used on Sephadex G-50 it is not surprising to find the peptides to be homogeneous on agarose. The consistently lower $R_f$ values on agarose as compared to Sephadex G-50 (see Table I) undoubtedly reflects the greater degree to which all the peptides penetrate the agarose matrix in the stationary aqueous phase. These lower values are in fact closer to the optimum recommended for partition columns, i.e., 0.3 or less.

The analgesic activities of the analogs as measured by the tail-flick method provided basis for comparing the potencies of the analgesic activity of the analogs to $β_h$-endorphin.

TABLE II

Amino Acid Analyses of Acid Hydrolysates of Synthetic β-Endorphin Analogs[a]

| Amino Acid | [$Sar^2$]-$β_c$-EP[b] | [$Ala^2$]-$β_c$-EP | [$D-Leu^2$]-$β_c$-EP | [$D-Lys^2$]-$β_c$-EP | [$Pro^5$]-$β_h$-EP | [$Leu^5$]-$β_h$-EP | [$D-Leu^5$]-$β_h$-EP | [$D-Ala^2$, $D-Leu^5$]-$β_h$-EP |
|---|---|---|---|---|---|---|---|---|
| Lys | 5.1 (5) | 4.8 (5) | 4.8 (5) | 5.7 (6) | 4.7 (5) | 4.8 (5) | 4.7 (5) | 4.8 (5) |
| His | 1.0 (1) | 0.9 (1) | 0.9 (1) | 0.9 (1) | | | | |
| Asp | 2.0 (2) | 2.1 (2) | 2.1 (1) | 2.1 (2) | 2.1 (2) | 2.1 (2) | 2.2 (2) | 2.2 (2) |
| Thr | 2.8 (3) | 2.8 (3) | 2.8 (3) | 2.9 (3) | 2.9 (3) | 2.8 (3) | 2.8 (3) | 2.9 (3) |
| Ser | 1.8 (2) | 1.8 (2) | 1.8 (2) | 1.9 (2) | 1.9 (2) | 1.8 (2) | 1.8 (2) | 1.8 (2) |
| Glu | 3.2 (3) | 3.1 (3) | 3.2 (3) | 3.2 (3) | 3.3 (3) | 3.1 (3) | 3.1 (3) | 3.2 (3) |
| Pro | 1.1 (1) | 1.0 (1) | 0.9 (1) | 1.1 (1) | 1.8 (2) | 1.0 (1) | 1.1 (1) | 0.9 (1) |
| Gly | 2.0 (2) | 2.3 (2) | 2.0 (2) | 2.1 (2) | 3.2 (3) | 3.0 (3) | 3.2 (3) | 2.1 (2) |
| Ala | 2.0 (2) | 3.1 (3) | 2.1 (2) | 1.9 (2) | 1.8 (2) | 2.1 (2) | 1.9 (2) | 3.1 (3) |
| Val | 1.0 (1) | 1.1 (1) | 1.1 (1) | 1.1 (1) | 1.1 (1) | 1.0 (1) | 1.1 (1) | 0.9 (1) |
| Met | 1.1 (1) | 1.0 (1) | 1.0 (1) | 1.0 (1) | | | | |
| Ile[c] | 1.2 (2) | 1.2 (2) | 1.3 (2) | 1.3 (2) | 1.4 (2) | 1.4 (2) | 1.4 (2) | 1.4 (2) |
| Leu | 1.9 (2) | 2.0 (2) | 3.1 (3) | 2.0 (2) | 2.0 (2) | 3.1 (3) | 3.0 (3) | 3.1 (3) |
| Tyr | 0.9 (1) | 1.0 (1) | 1.0 (1) | 0.9 (1) | 1.9 (2) | 2.0 (2) | 2.0 (2) | 2.0 (2) |
| Phe | 1.9 (2) | 1.9 (2) | 2.0 (2) | 1.9 (2) | 1.9 (2) | 2.0 (2) | 2.0 (2) | 2.1 (2) |

[a]Calculated values in parentheses.
[b]Sarcosine not determined.
[c]The low Ile values can be accounted for by the presence of the acid resistant Ile-Ile moiety.

Amino acid analyses shown in Table III were in agreement with values based upon the following considerations. In all cases $NH_2$-terminal tyrosine was released even in the presence of a D-amino acid in position 2. For [$D-Leu^2$] $β_c$-endorphin, the D-Leu-Gly-Phe moiety was partially resistant to attack while for [$D-Lys^2$] $β_c$-endorphin the D-Lys-Gly-Phe sequence was not attacked. In [$D-Leu^5$] $β_h$-endorphin the Gly-Phe-D-Leu-Thr-Ser-Glu-Lys segment was resistant to digestion and in [$D-Ala^2$, $D-Leu^5$] $β_h$-endorphin the D-Ala-Gly-Phe-D-Leu-Thr-Ser-Glu-Lys moiety was not attacked.

For analgesic assay, male ICR mice weighing 25–30 g (Simonsen Laboratories, Gilroy, CA.) were used. The analgesic properties of synthetic analogs were assessed

TABLE III

Amino Acid Analyses of Enzymic Hydrolysates of Synthetic β-Endorphin Analogs[a]

| Amino Acid | [$Ala^2$]-$β_c$-EP | [$D-Leu^2$]-$β_c$-EP | [$D-Lys^2$]-$β_c$-EP | [$Pro^5$]-$β_h$-EP | [$Leu^5$]-$β_h$-EP | [$D-Leu^5$]-$β_h$-EP | [$D-Ala^2$, $D-Leu^5$]-$β_h$-EP |
|---|---|---|---|---|---|---|---|
| Lys | 5.0 (5) | 4.9 (5) | 4.7 (5) | 5.0 (5) | 4.7 (5) | 4.0 (4) | 3.8 (4) |
| His | 0.9 (1) | 0.9 (1) | 0.8 (1) | | | | |

TABLE III-continued

Amino Acid Analyses of Enzymic Hydrolysates of Synthetic β-Endorphin Analogs[a]

| Amino Acid | [Ala²]-$\beta_c$-EP | [D-Leu²]-$\beta_c$-EP | [D-Lys²]-$\beta_c$-EP | [Pro⁵]-$\beta_h$-EP | [Leu⁵]-$\beta_h$-EP | [D-Leu⁵]-$\beta_h$-EP | [D-Ala², D-Leu⁵]-$\beta_h$-EP |
|---|---|---|---|---|---|---|---|
| Thr + Ser + Asn + Gln | 8.6 (9) | 9.0 (9) | 9.1 (9) | 8.1 (8) | 8.2 (8) | 6.3 (6) | 5.6 (6) |
| Glu | 1.0 (1) | 1.1 (1) | 1.1 (1) | 2.1 (2) | 2.2 (2) | 1.3 (1) | 1.2 (1) |
| Pro | 1.1 (1) | 1.0 (1) | 1.0 (1) | 1.9 (2) | 0.9 (1) | 1.0 (1) | 1.0 (1) |
| Gly | 2.3 (2) | 1.4 (1) | 1.2 (1) | 2.7 (3) | 3.2 (3) | 2.0 (2) | 1.0 (1) |
| Ala | 3.1 (3) | 1.9 (2) | 2.0 (2) | 2.0 (2) | 1.8 (2) | 1.9 (2) | 1.9 (2) |
| Val | 1.0 (1) | 1.2 (1) | 1.1 (1) | 1.2 (1) | 1.2 (1) | 1.1 (1) | 1.1 (1) |
| Met | 1.0 (1) | 1.0 (1) | 0.9 (1) | | | | |
| Ile | 1.9 (2) | 2.0 (2) | 1.9 (2) | 1.8 (2) | 1.7 (2) | 1.9 (2) | 1.8 (2) |
| Leu | 2.1 (2) | 2.3 (2) | 2.1 (2) | 2.1 (2) | 2.9 (3) | 2.2 (2) | 2.0 (2) |
| Tyr | 1.0 (1) | 1.1 (1) | 1.1 (1) | 2.2 (2) | 2.1 (2) | 2.0 (2) | 2.0 (2) |
| Phe | 2.0 (2) | 1.3 (1) | 1.1 (1) | 1.9 (2) | 1.9 (2) | 1.1 (1) | 1.1 (1) |

[a]Calculated values in parentheses were based on considerations explained in the text. The percentage hydrolysis of releasable amino acids was calculated to be 89–104% of the corresponding values for acid hydrolysis for all seven analogs recorded above.

All analogs showed decreases in potency with the most potent being [D-Leu²] $\beta_c$-endorphin which is half as potent as $\beta_h$-endorphin. Lower but still substantial activities in the range of 8 to 17% were shown by [Ala²]- and [D-Lys²] $\beta_c$-endorphin and by [Leu⁵]- and [D-Ala², D-Leu⁵] $\beta_h$-endorphin.

It is interesting that β-endorphin appears to be relatively tolerant to changes in the 2-position although the N-methyl amino acid sarcosine is evidently too drastic a replacement.

[Ala², Met⁵] enkephalinamide has been shown to be devoid of analgesic activity, while the [Ala²] $\beta_c$-endorphin analog of the present invention exhibits significant activity albeit to a lesser extent than the parent compound. Apparently, some activity in β-endorphin can be retained even with a reversal of configuration at the 2-position. Furthermore, bulkiness of the side-chain in this position as in [D-Leu²] $\beta_c$-endorphin and [D-Lys²] $\beta_c$-endorphin diminishes but does not abolish analgesic potency. The enkephalins appear to be quite sensitive to the nature of the side-chain placed in the 2-position. Thus far the evidence suggests β-endorphin to be less sensitive to alterations in this position than are the enkephalins to corresponding changes.

The [Leu⁵] $\beta_h$-endorphin is interesting if it is proven to exist naturally it would correspond to the endorphin form of [Leu⁵] enkephalin. Comparison of the analgesic activity of Met⁵-enkephalin with [Leu⁵] enkephalin has shown the former to have measurable but fleeting activity while the latter shows none. But a quantitative comparison is difficult since the responses to Met⁵-enkephalin are so close to control levels. In β-endorphin the replacement of Met⁵ by Leu decreases analgesic potency but clearly does not abolish it. However, when the configuration of the Leu⁵ residue is reversed to give [D-Leu⁵] $\beta_h$-endorphin, a drastic decrease in potency occurs. This parallels the change previously observed in going from $\beta_c$-endorphin to [D-Met⁵] $\beta_c$-endorphin.

When the 5-position is occupied by Pro a similar drastic decline is observed. This would appear to contrast with the enkephalins where Pro in position 5 increases activity. When the 2-position in [D-Leu⁵] $\beta_h$-endorphin is replaced by a D-Ala residue, considerable activity is restored but not to the level of the parent molecule. Simultaneous changes in position 2 and 5 of enkephalin have been reported to vastly increase analgesic activity even to the point where activity is observed through the intravenous route.

The β-endorphin analogs of the present invention can be employed as analgesic agents and as agents in the treatment of mental disease states such as schizophrenia and depression in the same manner as β-endorphin with dosage being adjusted for their relative potencies.

Sterile, stable dosage forms suitable for reconstitution for parenteral administration are obtained by filtering aqueous buffered solution of the desired compound of the invention through a sterilizing filter into sterile vials and then lyophilizing. The solid lyophilized product can be reconstituted at the time of use by the addition of sterile isotonic saline. Other parenteral dosage forms known in the art for the administration of peptides can also be used.

I claim:

1. A β-endorphin analog selected from the group consisting of [Ala²]-, [D-Leu²], [D-Lys²], [Leu⁵]-, and [D-Ala², D-Leu⁵]-β-endorphin, with the proviso that [Leu⁵] β-endorphin is essentially free of other pituitary peptides.

2. The β-endorphin analogs of claim 1 wherein said β-endorphin is human β-endorphin.

3. The human β-endorphin analog of claim 2 which is [Leu⁵]-$\beta_h$-endorphin.

4. The human β-endorphin analog of claim 2 which is [D-Ala², D-Leu⁵] $\beta_h$-endorphin.

5. The β-endorphin analogs of claim 1 wherein said β-endorphin is camel β-endorphin.

6. The camel β-endorphin analog of claim 5 which is [Ala²] $\beta_c$-endorphin.

* * * * *